(12) United States Patent
Rickman

(10) Patent No.: US 8,478,532 B2
(45) Date of Patent: Jul. 2, 2013

(54) TESTING ADDITIVES FOR PRODUCTION ENHANCEMENT TREATMENTS

(75) Inventor: Richard Dale Rickman, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/555,285

(22) Filed: Jul. 23, 2012

(65) Prior Publication Data

US 2012/0285231 A1 Nov. 15, 2012

Related U.S. Application Data

(63) Continuation of application No. 12/650,934, filed on Dec. 31, 2009, now Pat. No. 8,306,751.

(51) Int. Cl.
*G01V 9/00* (2006.01)

(52) U.S. Cl.
USPC .......................................................... 702/11

(58) Field of Classification Search
USPC .................. 702/11, 13, 14, 182–185, 188
See application file for complete search history.

(56) References Cited

U.S. PATENT DOCUMENTS

| | | | |
|---|---|---|---|
| 6,017,855 A | 1/2000 | Dawson et al. | |
| 6,267,893 B1 * | 7/2001 | Luxemburg | 210/723 |
| 6,383,990 B1 | 5/2002 | Dawson et al. | |
| 6,844,296 B2 | 1/2005 | Dawson et al. | |
| 7,012,044 B2 | 3/2006 | Dawson et al. | |
| 7,407,010 B2 | 8/2008 | Rickman et al. | |
| 7,448,451 B2 | 11/2008 | Nguyen et al. | |
| 7,500,521 B2 | 3/2009 | Nguyen et al. | |
| 2006/0219405 A1 | 10/2006 | Nguyen et al. | |
| 2006/0219408 A1 | 10/2006 | Nguyen et al. | |
| 2006/0240995 A1 | 10/2006 | Rickman et al. | |
| 2007/0187090 A1 | 8/2007 | Nguyen et al. | |
| 2007/0215354 A1 | 9/2007 | Rickman et al. | |
| 2007/0289781 A1 | 12/2007 | Rickman et al. | |
| 2008/0006405 A1 | 1/2008 | Rickman et al. | |
| 2008/0006406 A1 | 1/2008 | Nguyen et al. | |
| 2008/0128131 A1 | 6/2008 | Nguyen et al. | |
| 2009/0151943 A1 | 6/2009 | Nguyen et al. | |

OTHER PUBLICATIONS

"SandWedge® Conductivity Enhancement Service," Copyright 2007 Halliburton, 4 pages.

* cited by examiner

*Primary Examiner* — Edward Raymond
(74) *Attorney, Agent, or Firm* — Robert A. Kent; Fish & Richardson P.C.

(57) ABSTRACT

Fluid tests may be performed to determine suitability of an additive for a production enhancement treatment. In one aspect, a measuring device is used to determine a result of adding a sample of solid material to a test fluid that includes an additive. The result may include, for example, a change in surface tension, a change in contact angle, and/or another result. The measured result is used to determine the suitability of the additive for use in a stimulation treatment for a subterranean formation. For example, the additive may be determined suitable for use during a pad phase of a fracture treatment, during a proppant-laden phase of a fracture treatment, and/or for other phases and/or types of stimulation treatments.

24 Claims, 7 Drawing Sheets

TESTING ADDITIVES FOR PRODUCTION ENHANCEMENT TREATMENTS

CROSS REFERENCE TO RELATED APPLICATION

This application is a continuation and claims the benefit under 35 U.S.C. §120 of U.S. patent application Ser. No. 12,650,934, entitled "Testing Additives for Production Enhancement Treatments," filed Dec. 31, 2009, which is incorporated herein by reference in its entirety.

BACKGROUND

Oil and gas wells produce oil, gas and/or byproducts from underground reservoirs. Oil and gas reservoirs are formations of rock containing oil and/or gas. The type and properties of the rock may vary by reservoir and also within reservoirs. For example, the porosity and permeability of a reservoir rock may vary from reservoir to reservoir and from well to well in a reservoir. The porosity is the percentage of core volume, or void space, within the reservoir rock that can contain fluids. The permeability is a measure of the reservoir rock's ability to flow or transmit fluids.

Capillary pressure refers to a difference in pressure across a fluid interface in a capillary. Capillary pressures in a reservoir generally depend on the porosity and permeability of the rock as well as other properties of the rock and the fluids. Unconventional reservoirs, which may include shale reservoirs, tight gas reservoirs, and other types of low permeability reservoirs, typically exhibit high capillary pressures. High capillary pressures in a reservoir may lead to phase trapping rendering that phase immobile in the reservoir, which may inhibit or hinder production of resources.

Oil and gas production from a well may be stimulated by fracture, acid or other production enhancement treatments. In a fracture treatment, fluids are pumped downhole under high pressure to hydraulically fracture the reservoir rock in order to connect a larger portion of the reservoir to the wellbore. In some implementations, fracture fluids without proppants are injected into the formation to fracture the formation, and fracturing fluid with proppants are then pumped into the formation to hold the fractures open.

SUMMARY

In a general aspect, fluid testing techniques are used to identify fluids that are suitable for a production enhancement treatment.

In one aspect, a measuring device is used to determine a result of adding a sample of solid material to a test fluid that includes an additive. The suitability of the additive for use in a stimulation treatment for a subterranean formation is determined based at least in part on the result.

Some embodiments may include one or more of the following features. Determining the result includes using the measuring device to measure a first surface tension of the test fluid before adding the sample to the test fluid. Determining the result includes using the measuring device to measure a second surface tension of the test fluid after adding the sample to the test fluid. The result is the difference between the first surface tension and the second surface tension. The second surface tension is substantially equal to the first surface tension, and determining the suitability includes determining that the additive is suitable for a pad phase of the stimulation treatment. Determining the result includes using the measuring device to measure a first contact angle between the test fluid and a test surface before adding the sample to the test fluid. Determining the result includes using the measuring device to measure a second contact angle between the test fluid and the test surface after adding the sample to the test fluid. The response is a difference between the first contact angle and the second contact angle. The second contact angle is greater than the first contact angle, and determining the suitability includes determining that the additive is suitable for a proppant phase of the stimulation treatment. The test fluid is a first test fluid that includes a first concentration of the additive in a solvent, the sample is a first sample, and the result is a first result. The measuring device is used to determine a second result of adding a second sample of the solid material to a second test fluid that includes a second concentration of the additive and the solvent. The measuring device is used to determine a third result of adding a third sample of the solid material to a third test fluid that includes a third concentration of the additive and the solvent. The suitability is determined based on the first response, the second response, and the third response. The third concentration is the critical micelle concentration. The sample includes at least one of granular rock material, granular mineral material, graded sand, a proppant material, cuttings from the subterranean formation, or crushed material from the subterranean formation. Determining a suitability of the additive includes using a data processor to analyze the response. Determining a suitability of the additive includes determining that the additive is a non-adsorbing surfactant, a weakly-adsorbing surfactant, or a strongly-adsorbing surfactant.

In one aspect, information on an additive selected for treating a subterranean formation is received. The additive is selected for treating the subterranean formation based at least in part on a measured result of adding a sample of a solid material to a test fluid comprising the additive. The additive is injected into the subterranean formation through a well bore defined in the subterranean formation.

Some embodiments may include one or more of the following features. The sample of solid material includes crushed material and/or cuttings from the subterranean formation. The subterranean formation is a first subterranean formation, and the sample includes crushed material and/or cuttings from a second subterranean formation. The sample includes a proppant material, and injecting the additive includes injecting the additive and the proppant material into the subterranean formation. The sample includes a proppant material, and injecting the additive includes injecting the additive into a region of the subterranean formation where the proppant material resides. The additive is an additive selected based on the measured result of adding the sample to the test fluid including no change in a surface tension of the test fluid and/or the measured result of adding the sample to the test fluid including an increase in a contact angle of the test fluid and a test surface.

In one aspect, a system includes a fluid testing subsystem and a stimulation treatment subsystem. The fluid testing subsystem determines a suitability of an additive for a stimulation treatment. The suitability is determined based at least in part on a result of adding a sample of a solid material to a test fluid that includes the additive. The stimulation treatment subsystem applies the additive to a subterranean formation through a well bore defined in the subterranean formation.

Some embodiments may include one or more of the following features. The subterranean formation includes shale, and the well bore includes a horizontal well bore. The subterranean formation includes a formation matrix and a fracture network. The fluid testing subsystem includes a fluid container that receives a test fluid comprising the additive and the sample of solid material. The fluid testing subsystem includes a tensiometer that measures a surface tension of the test fluid. The fluid testing subsystem includes a contact angle goniometer that measures a contact angle between the test fluid and a test surface. The stimulation treatment subsystem includes a tubular conduit installed in the well bore, a pump that communicates a treatment fluid comprising the additive into the tubular conduit, and an outlet in the well bore that receives the treatment fluid from the tubular conduit and communicates the treatment fluid into the subterranean formation.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
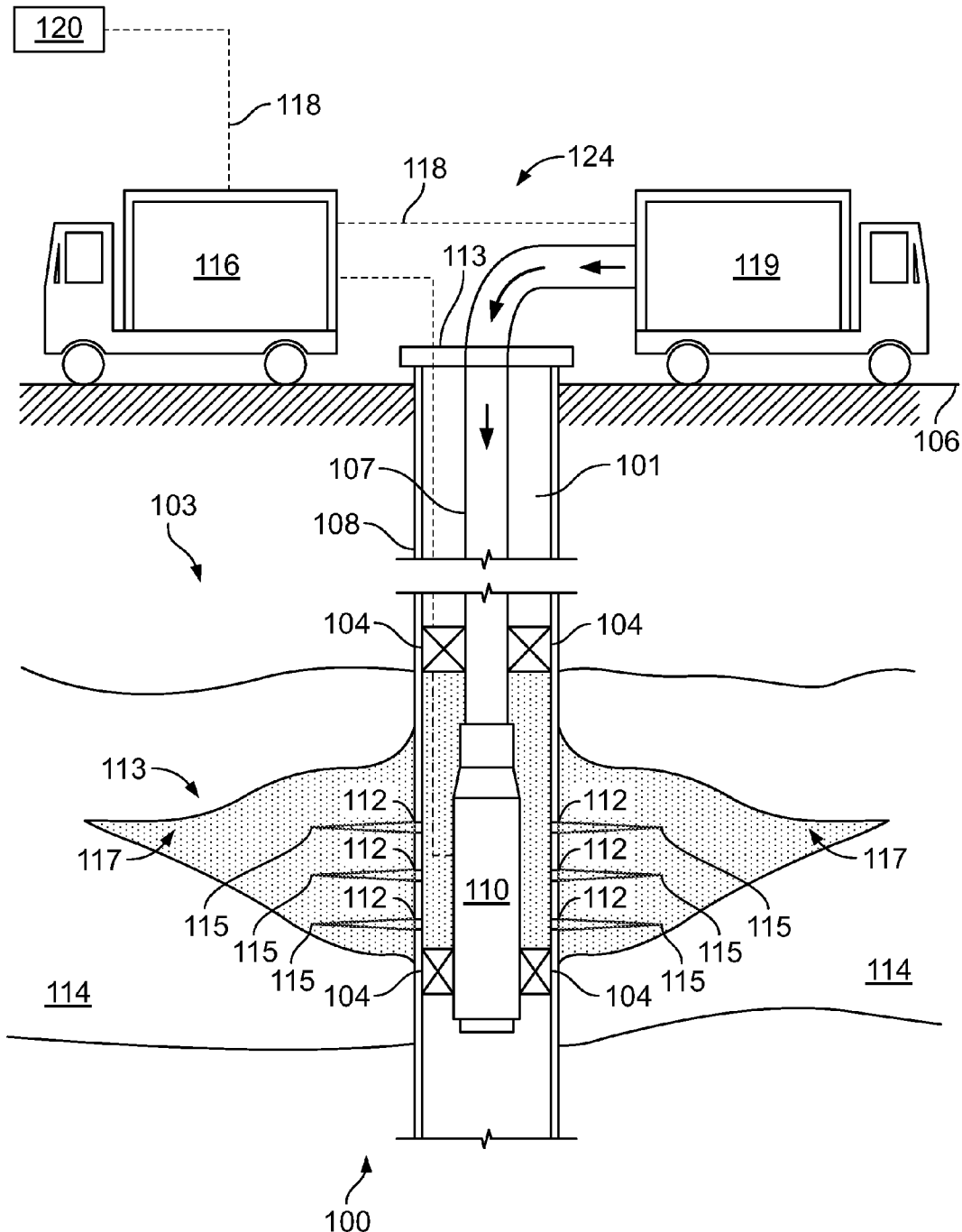
FIG. 1 is a diagram of an example well system.

FIG. 1 shows an example well system 100. The example well system 100 includes a well bore 101 in a subterranean region 103 beneath a surface 106. The well bore 101 may be used to apply a production enhancement treatment to and/or produce resources from the subterranean region 103; the well system 100 can include one or more additional wells used for treatment, production, observation, and/or other activities. The example well bore 101 intersects a subterranean formation 114, which may include a low permeability formation. Examples of low permeability formations include shale formations, coal formations, tight gas formations, and/or other types of formations. In some cases, low permeability rock may exhibit permeability less than one milliDarcy (mD). For example, permeability in shale formations may, in some instances, range from approximately $10^{-6}$ mD to approximately $10^{-3}$ mD; and permeability in a tight gas formation may, in some instances, range from approximately $10^{-3}$ mD to approximately $10^{-1}$ mD.

Permeability refers generally to the reservoir rock's ability to flow or transmit fluids. Absolute permeability refers to the rock's ability to flow or transmit a fluid when a single fluid is present in the rock. Effective permeability refers to the rock's ability to flow or transmit a particular fluid when other fluids are present in the rock. For example, a rock's effective permeability to hydrocarbons may refer to the rock's ability to flow or transmit hydrocarbons in the presence of water and/or other fluids. Low permeability formations typically exhibit high capillary pressures. Capillary pressure refers to a difference in pressure across a fluid interface in a capillary. High capillary pressures in a formation can cause phase trapping (e.g., water blockages, and/or other immobilized phases) in the formation. A phase trapping may be created by a fluid or a gas immobilized in the formation matrix. The immobilized phase may include water, hydrocarbon, gas, and/or others. Water blockages and other types of phase trapping may inhibit or hinder the migration of fluids through the formation matrix and thus have a negative impact on production.

The well system 100 of FIG. 1 may include, communicate with, and/or receive data from one or more fluid testing subsystems 120. A fluid testing subsystem 120 may test fluids for use in production enhancement treatments. For example, the fluid testing subsystem 120 may identify additives that promote fracturing fluid flowback and/or additives that remediate a trapped phase. In some implementations, the fluid testing subsystem 120 can be used to identify strongly adsorbing surfactants, weakly-adsorbing surfactants, non-adsorbing surfactants, and other types of additives. The fluid testing subsystem 120 can be a remote system that performs fluid tests at a location remote from a well site prior to treatment. The fluid testing subsystem 120 can be an on-site system that performs fluid tests near the well site. The fluid testing subsystem 120 can include both an on-site fluid testing subsystem and a remote fluid testing subsystem that operate independently or collaboratively. In some implementations, one or more constituents of a treatment fluid 117 is selected based on fluid tests performed by the fluid testing subsystem 120, and the treatment fluid 117 is injected into the formation 114 to enhance production.

In some implementations, the treatment fluid 117 enhances production by increasing all or part of the formation's effective permeability to hydrocarbons. For example, a surfactant may be included in the treatment fluid 117 based on the surfactant's tendency to adsorb to solid surfaces in the formation 114 (e.g., surfaces of proppant material in the formation 114) and thereby increase the rate at which hydrocarbons flow through the formation 114. In some examples, a strongly-adsorbing surfactant can modify the wettability of a solid surface, leading to less oil-wet (i.e., more water-wet) surfaces, which can improve transmission of hydrocarbons along the solid surface. An additive that strongly adsorbs to a solid surface may be identified by one or more fluid testing techniques. For example, a fluid testing subsystem 120 may perform one or more fluid tests to identify strongly-adsorbing surfactants for a stimulation treatment.

In some implementations, the treatment fluid 117 enhances production by reducing or maintaining capillary pressure in all or part of the formation 114. For example, a surfactant may be included in the treatment fluid 117 based on the surfactant's tendency not to adsorb to solid surfaces in the formation 114 (e.g., capillary surfaces in the formation 114). In some examples, a treatment fluid 117 that includes a weakly-adsorbing or non-adsorbing surfactant can be more efficiently recovered from the formation 114, and therefore the weakly-adsorbing or non-adsorbing surfactant prevents or reduces a tendency of the treatment fluid 117 to cause water blockages in the formation 114. An additive that weakly adsorbs (or does not adsorb) to a solid surface may be identified by one or more fluid testing techniques. For example, the fluid testing subsystem 120 may perform one or more fluid tests to identify weakly-adsorbing and/or non-adsorbing surfactants for a stimulation treatment.

The example fluid testing subsystem 120 can measure properties of test fluids and determine how the measured properties change when the test fluids are exposed to a mineral surface. For example, the fluid testing subsystem 120 can measure the response of a test fluid to adding proppant or rock formation material to the test fluid. In some implementations, the measured response may indicate a change or no change in surface tension of the test fluid, a change or no change in contact angle of the test fluid, and/or a different response. Multiple test fluids, each having a different concentration of an additive in a solvent, can be measured, and the measurements can be used to select fluids and/or additives for stimulation treatment to be applied to a subterranean formation. The fluid testing subsystem 120 may include the example fluid testing system 200 of FIG. 2 or a different fluid testing subsystem. The fluid testing subsystem 120 may be adapted to perform the example fluid testing techniques shown in FIGS. 3, 4, 5, 6, and 7 and/or other fluid testing techniques.

A stimulation treatment can be designed based on data generated by the fluid testing subsystem 120, and the stimulation treatment can be applied to the formation 114 through the well bore 101. For example, the stimulation treatment may include a fracture treatment applied to the subterranean formation 114 by a fracture treatment subsystem 124. The example fracture treatment subsystem 124 shown in FIG. 1 includes instrument trucks 116, pump trucks 119, and other equipment. The stimulation treatment may be applied through any suitable type of well bore and/or multiple well bores. The example well bore 101 shown in FIG. 1 includes a vertical well bore. A well bore may additionally or alternatively include one or more slant well bores, one or more horizontal well bores, one or more deviated well bores, and/or other types of well bores. A casing 108 may be cemented or otherwise secured in the well bore 101. Perforations 112 may be formed in the casing 108 to allow treatment fluids, proppants, and/or other materials to flow into the subterranean formation 114, and/or to allow oil, gas, by-products, and other materials to flow into the well bore 101 and be produced to the surface 106. Perforations 112 may be formed using shape charges, a perforating gun, and/or other tools. A stimulation treatment may be applied through an un-cased well bore and/or through an un-cased portion of a well bore.

The working string 107 disposed in the well bore 101 may include coiled tubing, sectioned pipe, and/or other types of conduit. A fracturing tool 110 may be coupled to the working string 107. In some cases, a fracture treatment and/or another type of stimulation treatment can be applied without use of a fracturing tool. The fracturing tool 110 can include a hydrajetting/fracturing tool and/or another type of fracturing tool. Example hydrajetting/fracturing tools include the SURGIFRAC tool (manufactured by HALLIBURTON), the COBRA FRAC tool (manufactured by HALLIBURTON), and/or others. The packers 104 shown in FIG. 1 seal the annulus of the well bore 101 above and below the subterranean formation 114. Packers 104 may include mechanical packers, fluid inflatable packers, sand packers, and/or other types of packers. Packers 104 may be placed in additional and/or different locations in the well bore 101.

The pump trucks 119 are coupled to the working string 107 at the surface 106. The pump trucks 119 may include mobile vehicles, immobile installations, skids, hoses, tubes, fluid tanks or reservoirs, pumps, valves, and/or other suitable structures and equipment. During operation, the pump trucks 119 pump treatment fluid 117 down the well bore 101, and the treatment fluid 117 is injected into the subterranean formation 114. The treatment fluid 117 may include a pad, proppants, a flush fluid, and/or other materials. For example, a fracture treatment may include a pad phase, where a pad (which typically includes fracture fluids without proppants) is pumped down the well bore and injected into the surrounding the formation to induce fracture. After the pad phase, the fracture treatment may include a subsequent proppant phase, where fracturing fluids containing proppants are pumped into the formation. The injected proppants may hold the fractures open to stimulate production from the formation. After the proppant phase, a fluid flush may be pumped into the well bore to clean the well bore of proppants and/or other materials. Additives may be included in the treatment fluid 117. The additives may lower the surface tension of the treatment fluid 117 and/or alter the contact angle of the treatment fluid 117 on mineral surfaces exposed to the fracturing fluid. The reduction in surface tension and/or alteration of the contact angle of the non-wetting phase on the treated mineral surfaces is desirable as both factors can reduce capillary pressures and thus minimize phase immobilization in the reservoir matrix.

The treatment fluid 117 may include a mixture of fluids, which may include one or more additives, and in some instances, a proppant material. The proppant, the fluids, the concentration of the fluid constituents, and/or other properties of the treatment fluid 117 may be selected based on a fluid test performed by the fluid testing subsystem 120. For example, the treatment fluid 117 may include a strongly-adsorbing surfactant, a weakly-adsorbing surfactant, a non-adsorbing surfactant, and/or another type of surfactant selected to enhance productivity from the subterranean formation 114. Different treatment fluids may be selected for each phase of production based on the fluid test results.

The instrument trucks 116 provided at the surface 106 may include mobile vehicles, immobile installations, and/or other suitable structures. The instrument trucks 116 may include a technical command center. The example instrument trucks 116 include a fracture control system that monitors and controls the fracture treatment. The fracture control subsystem may include a local computing system, and/or the fracture control subsystem may communicate with a remote computing subsystem. The fracture control system may control the pump trucks 119, fracturing tool 110, fluid valves, and/or other equipment used to apply the fracture treatment. The well system 100 may also include surface and down-hole sensors to measure pressure, rate, temperature and/or other parameters of treatment and/or production. The well system 100 may include pump controls and/or other types of controls for starting, stopping and/or otherwise controlling pumping as well as controls for selecting and/or otherwise controlling fluids pumped during the fracture treatment. The fracture control system in the instrument trucks 116 can communicate with the surface and/or subsurface sensor, instruments, and other equipment to monitor and control the fracture treatment.

The example instrument trucks 116 shown in FIG. 1 communicate with the pump trucks 119, the surface and subsurface instruments, the fluid testing subsystem 120, and/or other systems and subsystems through one or more communication links 118. The communication links 118 can include multiple uncoupled communication links and/or one or more networks of coupled communication links. The communication links 118 may include wired and/or wireless communications systems. For example, surface sensors and pump controls may communicate with the fracture control system through a wired or wireless link, down-hole sensors may communicate to a receiver at the surface 106 through a wired or wireless link, and the receiver may be coupled by a wired or wireless link to the fracture control system. As another example, the instrument trucks 116 may communicate with the pump trucks 119 and/or the remote fluid testing subsystem 120 via wired and/or wireless digital data communication networks, wired and/or wireless analog communication links, and/or other types of communication links.

The example subterranean formation 114 in FIG. 1 includes a fracture network 113. The fracture network 113 may include natural fractures, complex fractures, fractures 115 resulting from a fracture treatment applied to the subterranean formation 114, and/or other types of fractures. The fractures 115 resulting from a fracture treatment may include fractures resulting from a mini fracture test treatment, a regular or full fracture treatment, a follow-on fracture treatment, a re-fracture treatment, a final fracture treatment and/or another type of fracture treatment. The fracture network 113 may contain proppants injected into the subterranean formation 114 during the fracture treatment. The fracture network 113, which may include the propped fracture network, natural fractures, propagated fractures, etc., typically has a much higher permeability than the formation matrix. For example, the permeability of the fracture network 113 may range, in some cases from approximately $10^{-1}$ mD to approximately $10^2$ mD. In some examples, the permeability of the fracture network 113 is approximately eight to twelve orders of magnitude larger than the permeability of the formation matrix.

Thus, two regimes may be considered when choosing a surfactant/micro-emulsion package for hydraulic fracture stimulation in low permeability formations: the propped fracture regime and the formation matrix regime. In some low permeability formations, a strongly adsorbing surfactant in the fracture network enhances production by increasing the effective permeability of the fracture network to hydrocarbons, and a weakly adsorbing surfactant in the formation matrix enhances production by reducing water blockages in the formation matrix. As such, in some instances, different surfactant properties are desirable for the formation matrix regime and the propped fracture regime, and different surfactants can be used in different phases of a stimulation treatment to improve well performance. For example, in some instances, well performance may be maximized by choosing (1) a weakly-adsorbing or non-adsorbing surfactant for use in the pad phase of a treatment and (2) a strongly adsorbing surfactant for use in proppant-laden phase of the treatment. In the pad phase, the weakly-adsorbing or non-adsorbing surfactant may help maintain low surface tensions of both the injected and recovered fluids, which can reduce or minimize water blocks in the formation matrix. In the proppant-laden phase, the surfactant and/or the surfactant concentration can be chosen to ensure monolayer surfactant coverage on the proppant. Other stimulation treatment packages may use multiple different types of surfactants in one or more phase of treatment to improve production from both the formation matrix and the fracture network.

In one aspect of operation, the fracturing tool 110 is coupled to the working string 107 and positioned in the treatment well 101. The packers 104 are set to isolate the subterranean formation 114. The pump trucks 114 pump fracture fluid 117 down the working string 107 to the fracturing tool 110. The fracture fluid 117 exits the fracturing tool 110 and fractures the subterranean formation 114. In some implementations, the fracture fluid may include a fluid pad pumped down the well bore 101 to create or expand the fractures 115 in the subterranean formation 114, and proppants may then be pumped into the fracture network 113, followed by a fluid flush. The proppant may be pumped into the propagated fractures 115, a natural fracture network, a complex fracture network, and/or other types of fractures. In some implementations, the fracture treatment is performed in a different manner. For example, the fracture treatment may be applied through multiple well bores.

Figure 2:
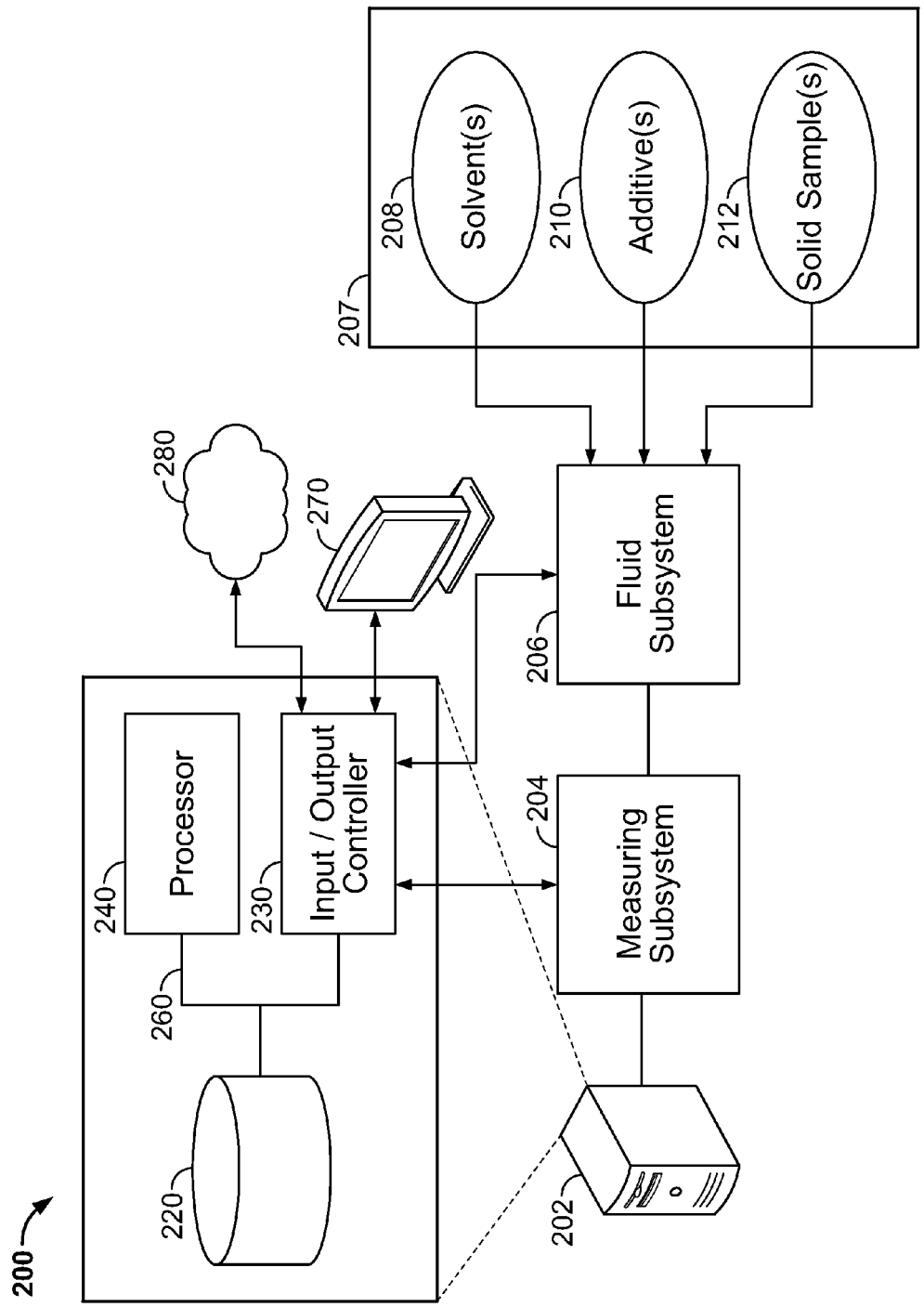
FIG. 2 is a diagram of an example fluid testing system.

FIG. 2 is a diagram of an example fluid testing system 200. The fluid testing system 200 can be the fluid testing subsystem 120 of FIG. 1. The fluid testing system 200 may be used to determine suitability of an additive for one or more phases of a stimulation treatment. For example, the fluid testing system 200 may be used to identify an additive to be applied to the formation matrix during a pad phase of treatment, an additive to be applied to the fracture network during a proppant-laden phase of treatment, and/or other additives. The fluid testing system 200 may be used to select a treatment fluid, or a component of a treatment fluid, based on physical properties of the (low permeability) formation matrix regime and/or properties of the (higher permeability) fracture network regime.

The difference in permeability between the formation matrix regime and the fracture network regime is typically accompanied by a concomitant difference in average pore radius between the regimes. For example, average pore radius may be related to permeability by the equation $\sqrt{k} \approx 2r$, where k is the permeability in mD and r is the average pore radius in micrometers (μm). From the propped fracture regime to the low permeability formation matrix regime, the average pore may radius may decrease by four to five orders of magnitude, in some cases.

The difference in permeability between the propped fracture regime and the formation matrix regime may lead to different capillary pressures in the two regimes. For example, capillary pressure can be expressed in terms of the permeability k as follows:

$$P_c = \frac{J(S_w) \cdot \sigma \cdot \cos\theta}{\left(\frac{k}{\phi}\right)^{1/2}} \quad (1)$$

where $J(S_w)$ is Leverett's J Function (a dimensionless unit tied to water saturation, typically having values between one and seven, with higher values indicating lower saturation), σ is the surface tension of a fluid in the capillary, θ is the contact angle of the fluid on the capillary walls, and φ is the fractional porosity. High capillary pressures, as may be exhibited in the formation matrix of a low permeability formation, can lead to phase trapping (e.g., water blockages, and/or phases) in the formation, for example, if reservoir pressure is insufficient to overcome the high capillary pressures. However, the problem of water blockage is less common, and in some cases may be disregarded, in the fracture network due to the significantly higher permeability of the fracture network.

Because the fracture network typically acts as a conduit that transmits resources from the formation to the wellbore, increasing the fracture network's effective permeability to hydrocarbons may improve production of hydrocarbons from the formation. The fracture network's effective permeability to hydrocarbons indicates the ability of the fracture network to transmit or flow hydrocarbons in the presence of other fluids in the fracture network. For example, hydrocarbons may flow more readily through a fracture network in the presence of a surfactant material that modifies the wettability of the proppant surface. In some instances, the fracture network's effective permeability to hydrocarbons should be maximized in order to optimize or improve production. Water saturation and/or surface wettability of the proppant in the fracture network can influence the fracture network's effective permeability to oil, gas, and aqueous fluids. For example, the permeability of untreated 70/170 mesh natural sand to kerosene is about 1.7 Darcies (D) and the permeability of untreated 70/170 mesh natural sand to water is about 7.3 D; but in 70/170 mesh natural sand that has been treated with a relatively strongly adsorbing surfactant, the effective permeability of kerosene is 7.6 D and the effective permeability of water is 5.7 D. The use of a strongly adsorbing surfactant may insure that the effective permeability modification is not short-lived, but rather a longer term effect.

Treating the proppant with strongly adsorbing surfactant can result in a contact angle θ closer to ninety (90) degrees. According to Equation 1 above, as θ approaches ninety (90) degrees, cos θ approaches zero (0), and capillary pressure approaches zero (0). In some implementations, the use of an adsorbing surfactant modifies the proppant surface to achieve a contact angle of approximately sixty (60) degrees, thus reducing the capillary pressure. While lower surface tensions may also contribute to lowering capillary pressure, from a practical standpoint, modulating the wettability may have better potential for minimizing the capillary pressure in the fracture network in some cases.

In the formation matrix regime, reducing the capillary pressure by using a strongly adsorbing surfactant to modify the contact angle may be more difficult or impractical due to the large surface area of the formation matrix. For example, in some instances, to sufficiently coat the formation matrix, high concentrations of the surfactant would be required, thus making the treatment costly, and possibly cost prohibitive. Treating the formation matrix with a strongly adsorbing surfactant that extends only a small distance (e.g., centimeters, millimeters, etc.) into the reservoir may, in some cases, have little or no effect in stimulating production. For example, in some shale or tight gas formations, the surfactant may extend much less than an inch into the reservoir. In some cases, capillary pressures in the formation matrix (and thus, the formation of water blockages in the formation matrix) can be reduced by returning the formation matrix surface to its pretreatment condition. The formation matrix surface may be returned to its pretreatment condition by extracting from the formation matrix any treatment fluids injected during a treatment.

When the surface tension of the injected fluid remains low or does not change appreciably upon injection into the formation matrix, the injected fluid may be more efficiently and/or more completely extracted from the formation matrix. The surface tension of the injected fluid may increase if surfactant adsorbs onto the mineral surface of the formation matrix. That is to say, the concentration of the surfactant in the fluid may be depleted as a result of the surfactant adsorbing to the formation matrix surface, and consequently, the surface tension of the fluid may rise. For example, the surfactant molecules in a solution of strongly adsorbing surfactants may preferentially coat the mineral surfaces, which may result in an increase in the surface tension of the fluid. Consequently, when an injected fluid contains strongly adsorbing surfactants, the injected fluid may be completely depleted of the surfactant due to adsorption, and capillary pressures can increase by a factor of two or three in some instances. For example, Table 1 below shows example values of surface tension for deionized water ("DI water") and deionized water with 0.2 percent concentration of surfactant ("DI water+0.2% Surfactant).

TABLE 1

Surface tensions for selected fluids

| Fluid | Surface Tension (dynes/cm) |
| --- | --- |
| DI water | 72 |
| DI water + 0.2% surfactant | 23.7 |

Based on the values from Table 1, when DI water is substituted for DI water+0.2% surfactant, the surface tension value in Equation 1 increases by a factor of approximately 2.5. Injecting surfactants that do not adsorb, and/or surfactants that adsorb minimally, onto mineral surfaces may reduce or prevent the surface tension from changing appreciably upon injection into the formation matrix, which may prevent an increase in capillary pressure in the formation matrix.

The example fluid testing system 200 includes a computing subsystem 202, a measuring subsystem 204, a fluid subsystem 206, test materials 207, and may include additional materials, equipment, and subsystems used to implement fluid testing techniques. All or part of the computing subsystems 202 and/or the measuring subsystems 204 may be integral with, separate from, and/or communicably coupled to the fluid subsystem 206. As shown in FIG. 2, the materials 207 may include solvents 208, additives 210, solid samples 212, and/or other materials.

The fluid subsystem 206 may include laboratory equipment for preparing and holding fluid samples during fluid tests. For example, the fluid subsystem 206 may include beakers, vials, pipettes, cylinders, fluid containers, glassware, plastics, metals, ceramics, slides and/or other equipment that can be used to transfer and contain fluid samples for testing. The fluid subsystem 206 may include stirrers, mixers, agitators, heating equipment, cooling equipment, pumps, hoses, tubing, and/or other equipment that can be used to prepare and mix fluid samples for testing. The fluid subsystem 206 may include micro-fluidic devices, macro-fluidic devices, and/or other devices of other appropriate sizes. The fluid subsystem 206 may include a condenser, a decanter, and/or a distiller for purifying or separating fluids. In some implementations, safety equipment, protective equipment, sanitary equipment, vents, hoods, and/or other types of equipment may also be used in connection with the fluid subsystem 206.

The fluid subsystem 206 is used to prepare fluid samples from the materials 207, which may include the solvents 208, the additives 210, the solid samples 212, and/or other materials. Solvents 208 may include stimulation treatment fluids and/or fracturing fluids. For example, the solvent 208 may include water, deionized water, brine, and/or other types of solvents. Additives 210 may include surfactant materials and/or other materials that can be added to the solvents 208. For example, the additives 210 may include surfactants materials that strongly or weakly adsorb to surfaces of one or more of the solid samples 212; the additives 210 may include other types of surfactants materials, such as those that do not adsorb to surfaces of the solid samples 212. In some implementations, the materials 207 include pre-mixed testing fluids that include mixtures of one or more additives 210 and/or one or more solvents 208. The additives may include cationic, anionic, nonionic, and/or zwitterionic surfactants. The additives may include other types of surfactant materials.

Examples of cationic surfactants include, but are not limited to, alkyl amines, alkyl diamines, alkyl ether amines, alkyl quaternary ammonium compounds, dialkyl quaternary ammonium compounds, ester quaternary ammonium compounds, erucyl bis(2-hydroxyethyl)methyl ammonium chlorides, bis(2-hydroxyethyl)erucylamine, erucyl trimethyl ammonium chlorides, N-methyl-N,N-bis(2-hydroxyethyl) rapeseed ammonium chlorides, oleyl methyl bis(hydroxyethyl)ammonium chlorides, octadecyl methyl bis(hydroxyethyl)ammonium bromides, octadecyl tris(hydroxyethyl) ammonium bromides, octadecyl dimethyl hydroxyethyl ammonium bromide, cetyl dimethyl hydroxyethyl ammonium bromide, cetyl methyl bis(hydroxyethyl)ammonium salicylates, cetyl methyl bis(hydroxyethyl)ammonium 3,4-dichlorobenzoates, cetyl tris(hydroxyethyl)ammonium iodides, cosyl dimethyl hydroxyethyl ammonium bromides, cosyl methyl bis(hydroxyethyl)ammonium chlorides, cosyl tris(hydroxyethyl)ammonium bromides, dicosyl dimethyl hydroxyethyl ammonium bromides, dicosyl methyl bis(hydroxyethyl)ammonium chlorides, dicosyl tris(hydroxyethyl)

ammonium bromides, hexadecyl ethyl bis(hydroxyethyl)ammonium chlorides, hexadecyl isopropyl bis(hydroxyethyl) ammonium iodide cetylaminos, N-octadecyl pyridinium chlorides, N-soya-N-ethyl morpholinium ethosulfates, methyl-1-oleyl amido ethyl-2-oleyl imidazolinium-methyl sulfates, methyl-1-tallow amido ethyl-2-tallow imidazolinium-methyl sulfates, trimethylcocoammonium chlorides, trimethyltallowammonium chlorides, dimethyldicocoammonium chlorides, bis(2-hydroxyethyl)tallow amines, bis(2-hydroxyethyl)coco-amines, cetylpyridinium chlorides, and any derivatives and combinations thereof. The term "derivative" includes any compound that is made from one of the listed compounds, for example, by replacing one atom in the listed compound with another atom or group of atoms, rearranging two or more atoms in the listed compound, ionizing one of the listed compounds, or creating a salt of one of the listed compounds.

Examples of anionic sufactants include, but are not limited to, sodium decylsulfates, sodium lauryl sulfates, alpha olefin sulfonates, alkylether sulfates, alkyl phosphonates, alkane sulfonates, fatty acid salts, arylsulfonic acid salts, lignosulfonates, alkylbenzene sulfonates, petroleum sulfonates, naphthalene sulfonates, olefin sulfonates, alkyl sulfates, sulfated natural fats and oils, sulfated fatty acids, particularly sulfated oleic acid, sulfated alkanolamides, sulfated esters, sulfated alkyl phenols, sulfated alcohols, 2-sulfoethy esters of fatty acids, monoalkylsulfosuccinates, dialkyl sulfosuccinates, polyethoxy carboxylic acids, acylated protein hydrolysates, N-acylsarcosinates, alkyl carboxylic acids, cycloalkyl carboxylic acids, aryl carboxylic acids, alkyl phosphates, alkyl thiophosphates, alkyl polyphosphates, ethoxylated phosphate esters, and any derivitatives and combinations thereof.

Examples of zwitterionic surfactants include alkyl betaines, alkyl amido betaines, alkyl imidazolines, alkyl amine oxides, alkyl quaternary ammonium carboxylates, and any derivatives and combinations thereof.

Solid samples 212 may include rocks, minerals, sand, proppants, materials extracted from a subterranean formation or an outcropping, and/or other types of solid materials. The solid samples 212 may include granular rock material, granular mineral material, graded sand, proppant materials, crushed material from a subterranean formation, cuttings from a subterranean formation, and/or other types of solid materials. For example, the solid samples 212 may include sand, granite, sandstone, shale, limestone, and/or other proppant materials. The fluid testing system 200 may include a crusher for crushing solid samples, a mortar, a pestle, a screen, a sifter, and/or other types of equipment for preparing granulated samples. In some implementations, a solid sample 212 may include solid grains in a specified range of sizes, and/or solid grains corresponding to a specified size distribution.

The measuring subsystem 204 may include one or more measuring devices that measures properties of the materials 207 before and/or after the materials 207 are combined in the fluid subsystem 206. The measuring subsystem 204 may include digital, analog, electronic, pneumatic, mechanical, chemical, and/or other types of measuring devices. The measuring subsystem 204 may include micro-fluidic measuring devices, macro-fluidic measuring devices, and/or measuring devices of any appropriate size. The measuring subsystem 204 may include devices for measuring temperature, volume, pressure, surface tension, surface energy, mass, weight, contact angle, length, force, pH, flow rate, electrical properties and/or other properties. The measuring subsystem 204 may include, for example, scales, balances, thermometers, thermocouples, tensiometers, goniometers, graduated cylinders, measuring cups, transducers, timing instruments, force gauges, pressure gauges, and/or other devices. The measuring subsystem 204 may include manually operated and/or automated measuring devices.

In some implementations, the measuring subsystem 204 includes a test surface and a contact angle goniometer that measures a contact angle between a liquid and the test surface. The test surface may include a flat surface, such as, for example, a test slide or another type of surface. The test surface may include a glass, ceramic, plastic, mineral, and/or other materials. The test surface may include a curved surface, such as, for example, a tube, a pipette, or another type of curved surface. In some implementations, the measuring subsystem 204 includes a tensiometer that measures a surface tension of a liquid sample.

The computing subsystem 202 may receive input data and generate output data. The computing subsystem 202 may include any of various types of devices, including, but not limited to, a personal computer system, desktop computer, laptop, notebook, mainframe computer system, handheld computer, workstation, graphing calculator, network computer, application server, storage device, a measuring device, and/or any type of computing or electronic device. The computing subsystem 202 may include measurement software, data plotting software, data analysis software, and/or other types of software. For example, the computing subsystem may include National Instruments LabVIEW software, the MathWorks MATLAB software, Microsoft Excel spreadsheet software, and/or other data analysis software.

The example computing subsystem 202 includes a processor 240, a memory 220, and input/output controllers 230 communicably coupled by a bus 260. The memory 220 can include, for example, a random access memory (RAM), a storage device (e.g., a writable read-only memory (ROM) and/or others), a hard disk, and/or another type of storage medium. The memory 220 can store instructions (e.g., computer code) associated with an operating system, computer applications, and/or other resources. The memory 220 can also store application data and data objects that can be interpreted by one or more applications and/or virtual machines running on the computing subsystem 202. The computing subsystem 202 can be preprogrammed and/or it can be programmed (and reprogrammed) by loading a program from another source (e.g., from a CD-ROM, from another computer device through a data network, and/or in another manner). The data stored in the memory 220 may include information received from the measuring subsystem 204 and/or from the testing subsystem 206, which may include raw data and/or signals, measured values, test result values, and/or other types of data. For example, the data stored in the memory 220 may include measurements of surface tension, contact angle, volume, temperature, fluid concentration, time, and/or other types of measurements.

The input/output controllers 230 may be coupled to input/output devices (e.g., a monitor 270, a printer, a mouse, a keyboard, and/or other input/output devices), the measurement subsystem 204, the fluid subsystem 206, a data communication network 280, and/or other systems and subsystems. The input/output devices receive and transmit data in analog or digital form over communication links such as a serial link, wireless link (e.g., infrared, radio frequency, and/or others), parallel link, and/or another type of link. The network 280 can include any type of data communication network. For example, the network 280 can include a wireless and/or a wired network, a Local Area Network (LAN), a Wide Area Network (WAN), a private network, a public network (such as the Internet), a WiFi network, a network that includes a satellite link, and/or another type of data communication network.

In one aspect of operation, multiple test fluids are prepared using the fluid subsystem 206. For example, each test fluid may be prepared in a separate container. Each test fluid may include a different concentration of a solvent material 208 and an additive material 210. For example, each test fluid may be prepared by mixing a specific amount of additive 210 and solvent 208 in a test container. An initial value of a property of each test fluid is measured using the measuring subsystem 204. For example, an initial surface tension or and/or contact angle may be measured for each test fluid. Data values for the initial measurements are stored in the memory 220. A sample of solid material 212 is added to each test fluid in the fluid subsystem 206. After the solid material is added, one or more subsequent values of the property are measured for each test fluid using the measuring subsystem 204. For example, one or more subsequent surface tension measurements and/or contact angle measurements may be taken for each test fluid. Data values for the subsequent measurements are stored in the memory 220. The processor 240 may execute instructions to analyze the measurement data stored in the memory 220. For example, the processor 240 may determine a change in the measured property, a change in time, and/or other values. The measured data and/or the results of data analysis may be displayed on the monitor 270, stored in the memory 220, communicated over the network 280, and/or further processed.

In some implementations, a surfactant selected for proppant-laden stages of treatment has a contact angle greater than or equal to forty degrees (i.e., $\theta \geq 40°$), which may increase the effective permeability of hydrocarbons in the fracture network. In some implementations, the surfactant for proppant-laden stages has multiple cationic sites to insure a relatively permanent bond to the proppant surface. In some implementations, a weakly-adsorbing or non-adsorbing surfactant may also be included in the proppant-laden stages to compensate for the leak-off of this fluid into the formation.

Figure 3:
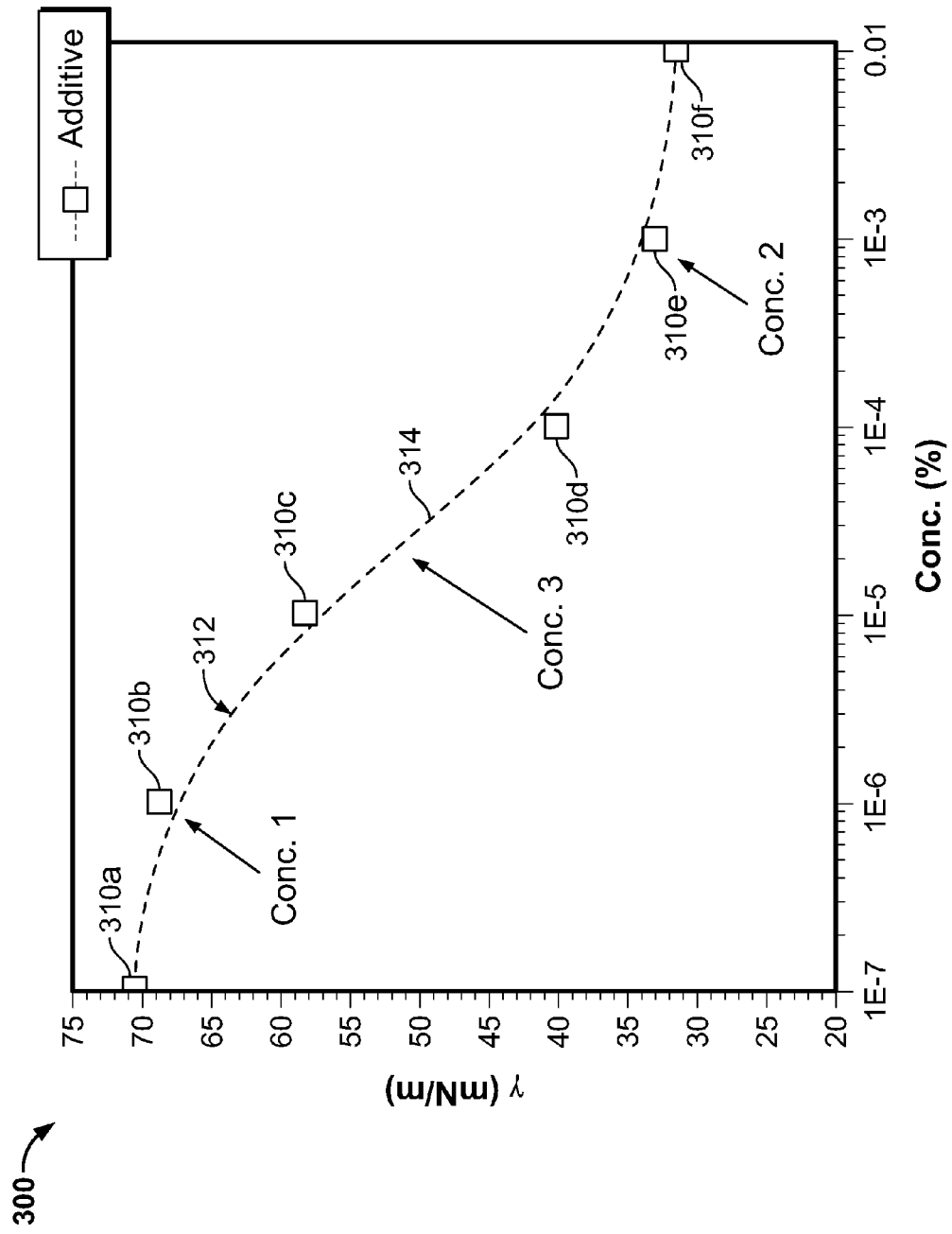
FIG. 3 is a plot of example data from a fluid test.
Figure 4:
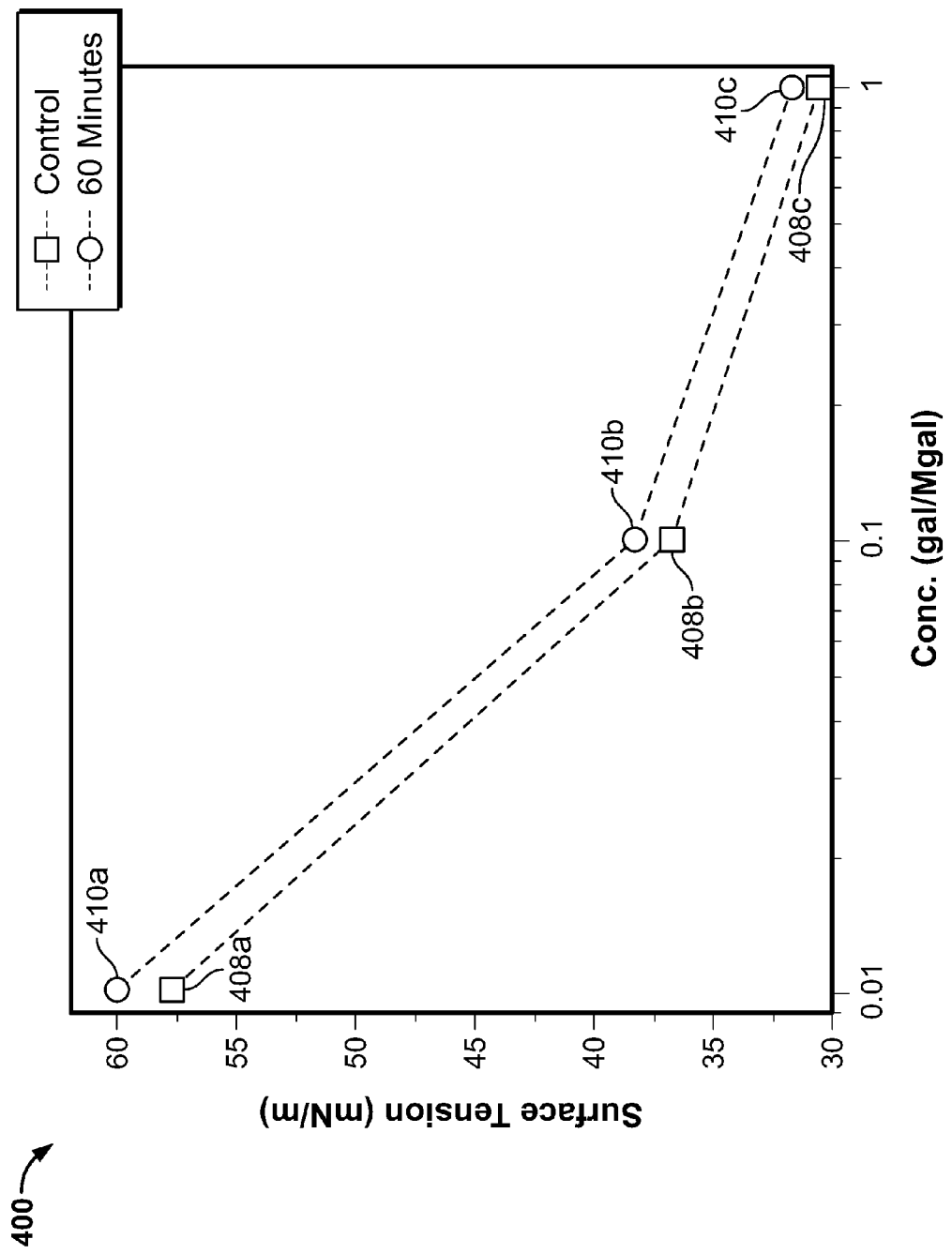
FIG. 4 is a plot of example data from a fluid test.

FIGS. 3 and 4 show data from an example fluid test. The example fluid test shown in FIGS. 3 and 4 can be used to identify a treatment fluid that will retain low surface tension in a formation matrix of a subterranean formation. In the examples shown, the additive is gas perm 1000, the solvent is water, and the solid material is 100 mesh sand. Other types of fluids and/or solid materials may be used. To begin the example fluid test, the surface tensions of fluids with different concentrations of an additive are measured. For example, FIG. 3 is a plot 300 of surface tension versus additive concentration. Percent concentrations of the additive are represented in log scale on the horizontal axis of the plot 300, and surface tensions in units of millinewtons per meter (mN/m) are represented in linear scale on the vertical axis of the plot 300. The square data points 310a, 310b, 310c, 310d, 310e, and 310f (collectively 310) represent measured surface tension values. Based on the measured values 310, surface tension as a function of additive concentration can be determined. The dotted line 312 represents a best-fit function of surface tension versus additive concentration.

Continuing the example fluid test, the data points 310 and/or the best-fit function can be used to identify three concentrations of solution to be tested. The three concentrations chosen for testing in the example shown are identified as "Conc. 1," "Conc. 2," and "Conc. 3" on the plot 300. The first concentration ("Conc. 1") is the lowest concentration at which a measurable decrease in surface tension is observed in the data. The third concentration ("Conc. 3") is the critical micelle concentration. The critical micelle concentration ("CMC") is the concentration at which micelles spontaneously form in the test fluid. The CMC may be determined based on visual inspection, by measurement, by an automated data analysis, and/or by another technique. The second concentration ("Conc. 2") is a concentration intermediate the first and third concentrations. The three concentrations may be chosen so as to maximize the sensitivity of subsequent measurements. A different number of test concentrations may be selected based on the same and/or different criteria.

Continuing the example fluid test, three test fluids are prepared; each prepared test fluid has one of the three chosen concentrations. That is to say, one of the test fluids is a mixture of the additive at the first concentration ("Conc. 1"); one of the test fluids is a mixture of the additive at the second concentration ("Conc. 2"); one of the test fluids is a mixture of the additive at the third concentration ("Conc. 3"). The surface tension of the three test fluids is measured and used as a baseline or control measurement. For example, FIG. 4 shows a plot 400 of surface tension versus additive concentration. Concentrations of the additive in units of gallon per thousand gallons (gal/Mgal) are represented in log scale on the horizontal axis of the plot 400, and surface tensions in units of mN/m are represented in linear scale on the vertical axis of the plot 400. The square data points 408a, 408b, and 408c represent the baseline measurements.

Continuing the example fluid test, crushed formation material (e.g., granite, shale, sandstone, coal, and/or others) and/or proppant material (e.g., graded sand, and/or others) are added to each of the three test fluids. The surface tension for each test fluid is recorded as a function of time until no measurable change is recorded. In the example fluid test, the surface tension of each test fluid reached a steady value before sixty (60) minutes from the time that the solid sample was added. The circle data points 410a, 410b, and 410c represent the surface tension measurements after sixty (60) minutes. The difference between the baseline surface tension measurement and the subsequent surface tension measurement for each test fluid represents the test fluid's response to adding the sample of solid material. For example, the difference between the data points 408a and 410a represents a result of adding the sample of solid material to the first test fluid; the difference between the data points 408b and 410b represents a result of adding the sample of solid material to the second test fluid; and the difference between the data points 408c and 410c represents a result of adding the sample of solid material to the third test fluid.

The response of each test fluid can be used to determine the additive's suitability for a stimulation treatment. For example, the additive may be selected for a stimulation treatment based on whether and/or how much the surface tension changes in response to adding the sample of solid material. An additive may be selected for a stimulation treatment based on the surface tension changing less than a threshold amount in response to adding the sample of solid material. An additive may be selected for a stimulation treatment based on the surface tension demonstrating no measurable change in response to adding the sample of solid material. No measurable change in surface tension may indicate that there was no appreciable adsorption of the additive to the added solid material and that the additive remained in solution serving to maintain the desired surface tension.

Other fluid tests may be conducted to determine suitability of an additive for a stimulation treatment. One example alternative fluid test may be used to identify an additive that will strongly adsorb to a proppant material and reduce a fluid contact angle in a fracture system of a subterranean formation. For example, in some implementations, in addition to measuring the initial surface tension for each of the three test fluids, an initial contact angle is measured for each of the three test fluids, and the initial contact angles serve as the baseline measurement. A contact angle for a test fluid may be measured, for example, by immersing a test slide in the test fluid for a period of time and measuring the resulting contact angle between the test surface and the surface of the test fluid. After solid material has been added and the surface tension has reached a steady value (e.g., after sixty (60) seconds, or another time period), the liquid test fluid is decanted from the mixture and the contact angle of the liquid is measured again. An additive may be selected for a stimulation treatment based on differences between the baseline contact angle measurement and the subsequent contact angle measurement. For example, an additive may be selected for a stimulation treatment based on the contact angle demonstrating a measurable reduction in response to adding the sample of solid material; an additive may be selected based on the contact angle being reduced by at least a threshold amount. A reduction in contact angle may indicate that the additive adsorbed to surface of the solid material.

Figure 5:
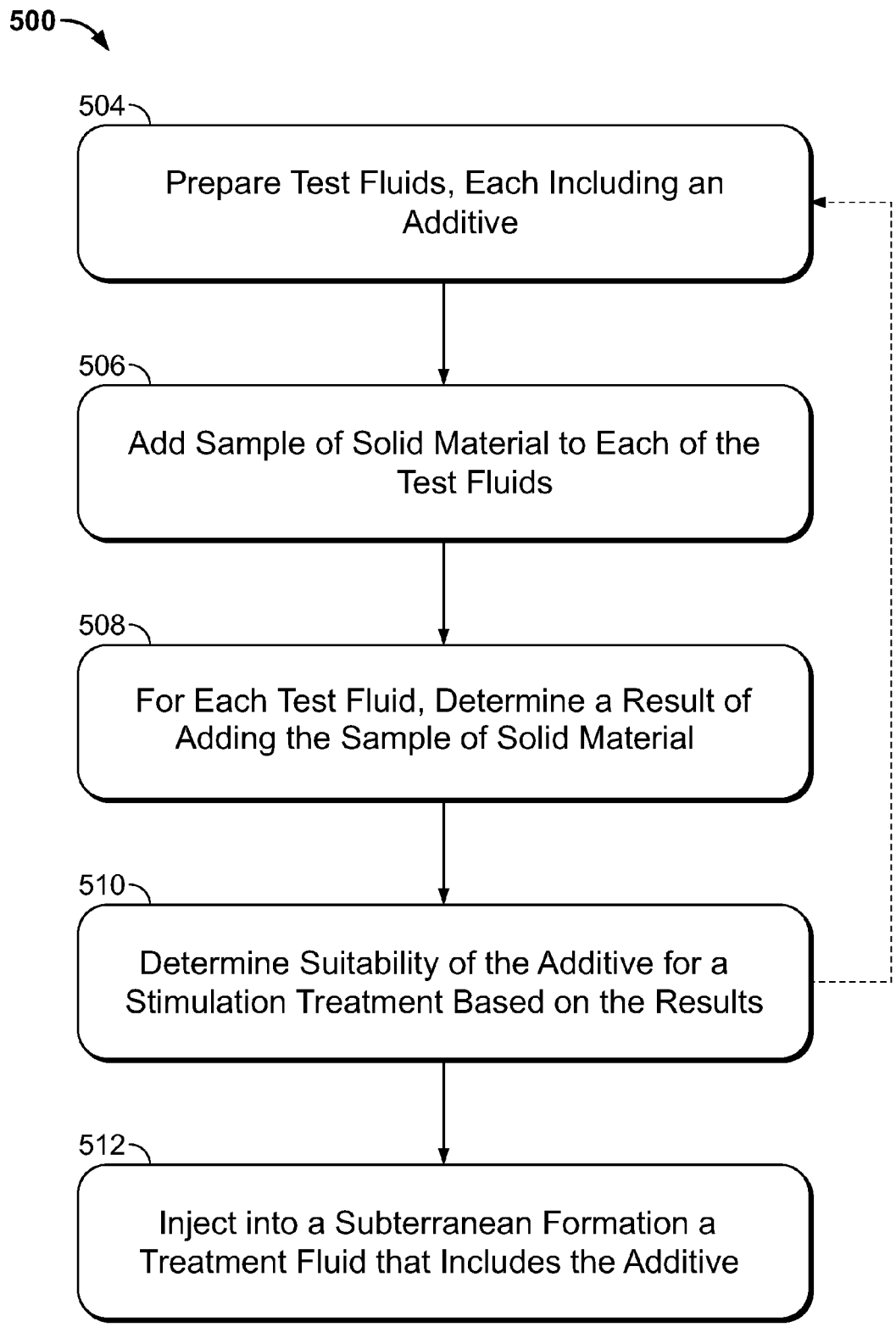
FIG. 5 is a flow chart of an example technique for applying a hydraulic treatment to a subterranean formation.

FIG. 5 is a flow chart of an example process 500 for applying a stimulation treatment to a subterranean formation. All or some of the operations of the example process 500 may be implemented using the example well system 100 of FIG. 1 and/or another system. In some implementations, the process 500 includes fewer, additional, and/or different operations performed in the same or a different order.

At 504, multiple test fluids are prepared; each test fluid includes an additive. The additive may include, for example, a surfactant material to be tested. In some implementations, each test fluid is prepared in a separate beaker or other type of fluid container. In some implementations, each test fluid includes a different concentration of the additive in a solvent fluid. Initial measurements of each test fluid are made before adding solid material to each test fluid.

At 506, a sample of solid material is added to each of the test fluids. The sample of solid material may include granular rock material, granular mineral material, graded sand, a proppant material, cuttings from a subterranean formation, crushed material from a subterranean formation, and/or another solid material. The mineral composition of the sample of solid material may be selected based on a mineral composition of a subterranean formation, a mineral composition of a proppant material, and/or other factors.

At 508, a result of adding the sample of solid material is determined for each test fluid. The result may be determined using a measuring device, such as, for example, a tensiometer, a test slide, and/or another device. For example, determining a result of adding the sample of solid material may include determining a difference between an initial surface tension and a final surface tension, determining a difference between an initial surface energy and a final surface energy, determining a difference in an initial contact angle and a final contact angle, determining a difference in an initial surface wettability and a final surface wettability, and/or determining another difference. Moreover, determining a result of adding the sample of solid material may include determining a change or no measurable change in surface tension, determining a change or no measurable change in surface energy, determining a change or no measurable change in contact angle, determining a change or no measurable change in surface wettability, and/or making another determination. The result of adding the solid material to a test fluid may be determined by a computing subsystem. For example, measured values may be received by the computing system, and the computing system may include logic that identifies the result based on the received values.

Based on the response, it may be determined that the additive is not suitable for a stimulation treatment. For example, a response that includes a change in surface tension may indicate that the additive is an adsorbing surfactant that is not suitable for a treatment where a non-adsorbing surfactant is desired. As another example, a response that includes no measurable change, or only a small change, in contact angle may indicate that the additive is a non-adsorbing or weakly-adsorbing surfactant that is not suitable for a treatment where a strongly-adsorbing surfactant is desired. When it is determined that the additive is not suitable for a stimulation treatment, the process 500 may terminate, or may continue at 504 with testing a new additive.

Based on the response, it may be determined that the additive is suitable for a stimulation treatment. For example, a response that includes no measurable change, or only a small change, in surface tension may indicate that the additive is a non-adsorbing surfactant that is suitable for treating the formation matrix during a pad phase of a stimulation treatment. As another example, a response that includes a decrease in contact angle may indicate that the additive is an adsorbing surfactant that is suitable for treating a fracture system during a proppant phase of a stimulation treatment. When it is determined that the additive is suitable for a stimulation treatment, the process 500 may continue at 510.

At 510, an additive is selected for a stimulation treatment based on the results. An additive may be selected for a stimulation treatment based on the suitability of the additive for a given phase of a stimulation treatment in a given subterranean formation and/or with a given proppant material. For example, if the solid material added to the test fluid (at 506) includes material extracted from a particular subterranean formation, the test results may indicate how the measured properties of the test fluid will be behave in the particular subterranean formation or a similar formation. As another example, if the solid material added to the test fluid (at 506) includes a particular proppant, the test results may indicate how the measured properties of the test fluid will be behave in a subterranean formation that includes the particular proppant.

At 512, a treatment fluid containing the additive is injected into a subterranean formation. The treatment fluid may be applied to the subterranean formation by a fracture treatment subsystem or another type of stimulation treatment subsystem. The stimulation treatment subsystem may include a tubular conduit installed in a well bore defined in the subterranean formation. The treatment fluid may be communicated by a pump into the tubular conduit. The treatment fluid may be communicated through the tubular conduit and into the formation through an outlet, such as, for example, a perforation in the tubular conduit or another type of outlet.

Figure 6:
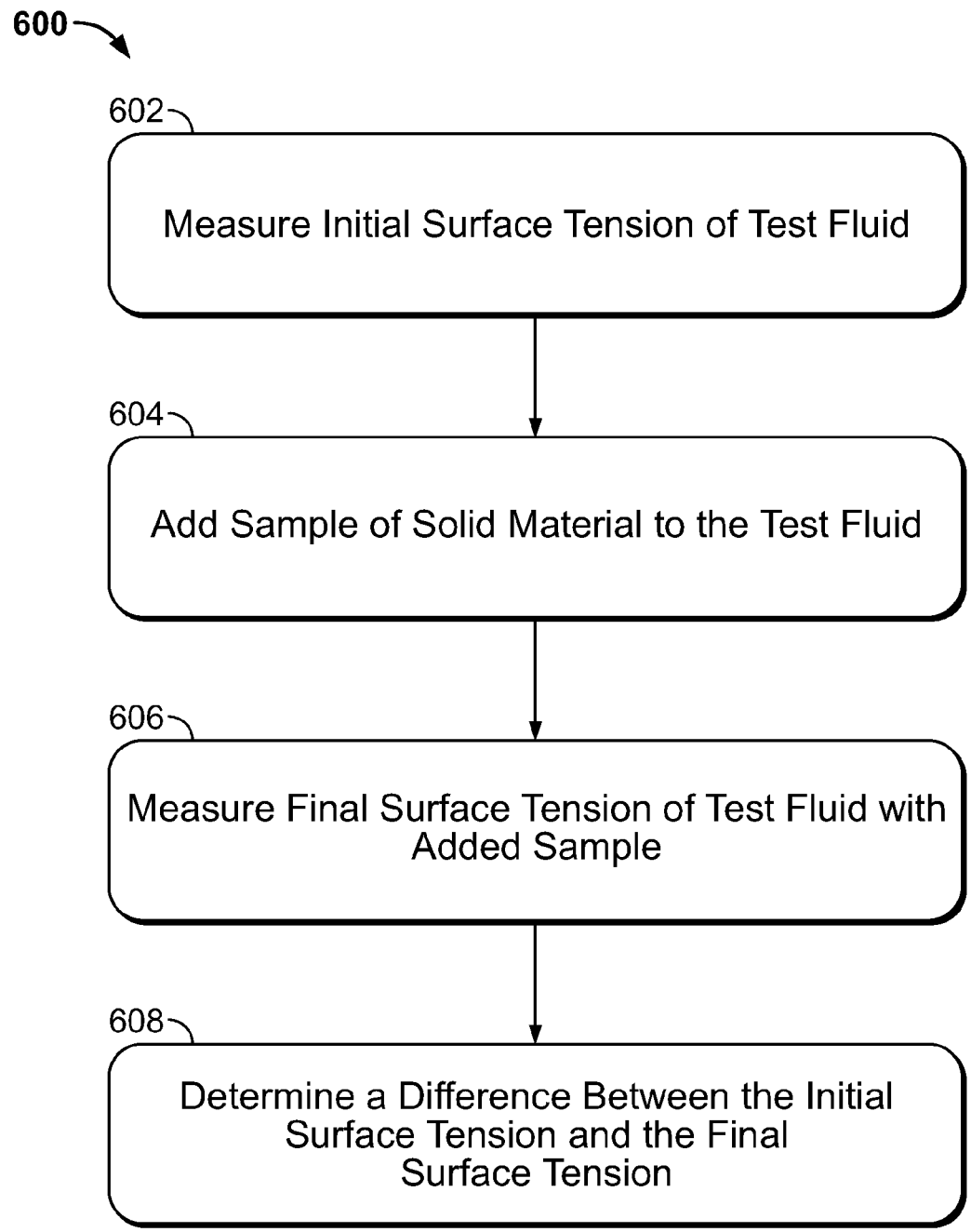
FIG. 6 is a flow chart of an example fluid testing technique.

FIG. 6 is a flow chart of an example fluid testing process 600. All or some of the operations of the example process 600 may be implemented using the example fluid testing system 200 of FIG. 2 and/or another system. In some implementations, the process 600 includes fewer, additional, and/or different operations performed in the same or a different order.

At 602, an initial surface tension of a test fluid is measured. The test fluid includes a surfactant. At 604, a sample of solid material is added to the test fluid. The solid material may include crushed material and/or cuttings from a subterranean formation, proppant material, and/or other types of solids. The resulting mixture may be stirred, mixed, or agitated. At 606, a final surface tension of the test fluid is measured. The final surface tension may be measured one or more times, after a predetermined amount of time, after the surface tension has reached a steady state, and/or after a different amount of time. At 608, a difference between the initial surface tension and a final surface tension is determined. The difference may be used to determine whether the surfactant is suitable for a stimulation treatment. Based on the measured difference, the surfactant may be used, for example, in a pad phase, a proppant phase, and/or a flush phase of a stimulation treatment. For example, if the difference is zero or immeasurably small, the surfactant may be used to treat a formation matrix during a pad phase. As another example, if the difference is zero or immeasurably small, the surfactant may be used to treat a formation matrix during a proppant-laden phase of treatment.

Figure 7:
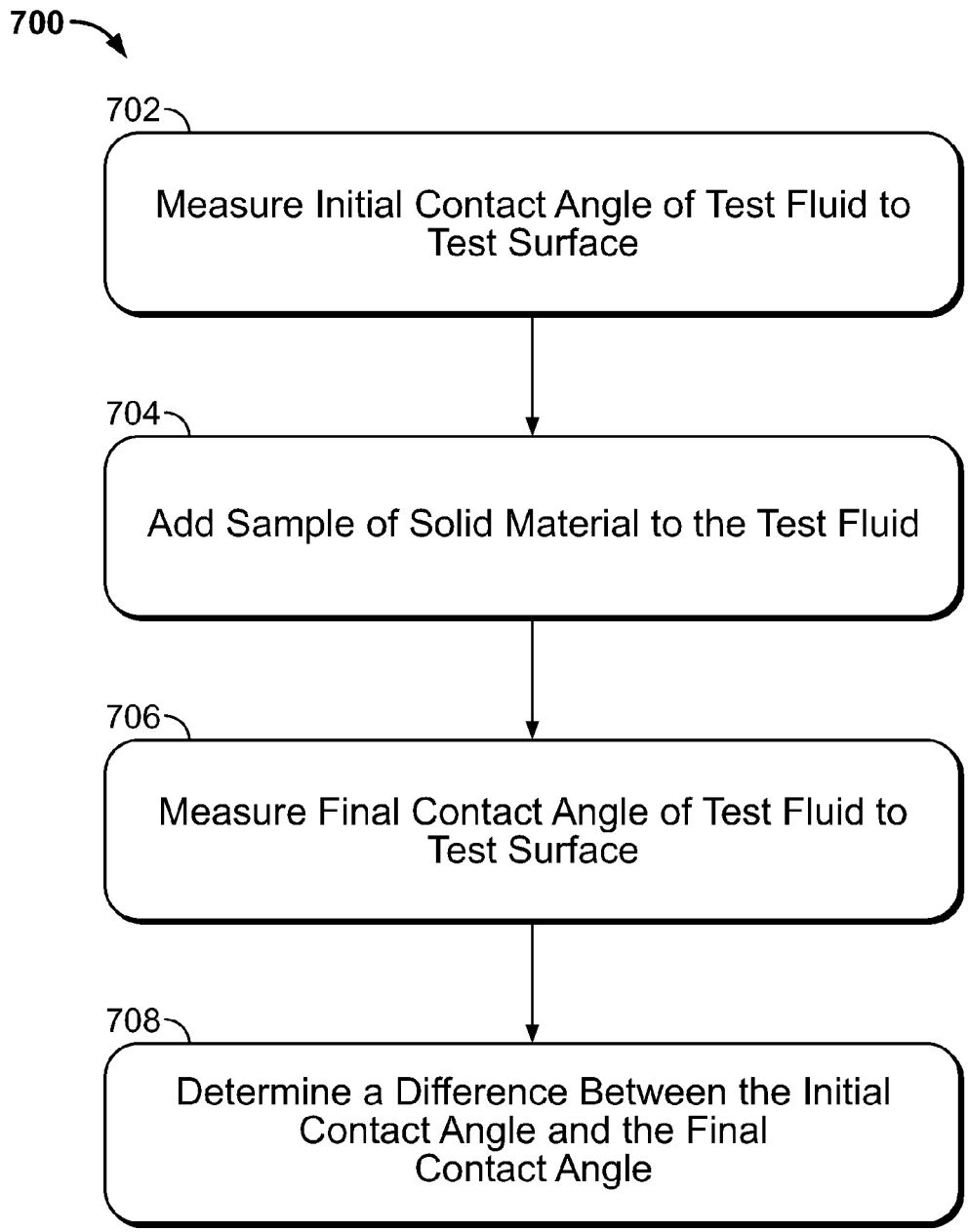
FIG. 7 is a flow chart of another example fluid testing technique.

FIG. 7 is a flow chart of another example fluid testing process 700. All or some of the operations of the example process 700 may be implemented using the example fluid testing system 200 of FIG. 2 and/or another system. In some implementations, the process 600 includes fewer, additional, and/or different operations performed in the same or a different order.

At 702, an initial contact angle between a test fluid and a test surface is measured. The test fluid includes a surfactant material. An initial surface tension may also be measured. At 704, a sample of solid material is added to the test fluid. The solid material may include crushed material and/or cuttings from a subterranean formation, proppant material, and/or other types of solids. The resulting mixture may be stirred, mixed, or agitated. The surface tension of the mixture may be monitored.

At 706, a final contact angle between the test fluid and the test surface is measured. The final contact angle may be measured one or more times, after a predetermined amount of time, after the surface tension has reached a steady state, and/or after a different amount of time. The final contact angle may be measured after the liquid of the test fluid is filtered, decanted, or otherwise separated from the solid material. The final contact angle may be measured using the same or a different test surface as the initial contact angle.

At 708, a difference between the initial contact angle and the final contact angle is determined. The difference may be used to determine whether the surfactant is suitable for a stimulation treatment. Based on the measured difference, the surfactant may be used, for example, in a pad phase, a proppant phase, and/or a flush phase of a stimulation treatment. For example, if the difference indicates a reduction of the contact angle as a result of adding the solid material, the surfactant may be used to treat a fracture system during a proppant phase.

Some embodiments of subject matter and operations described in this specification can be implemented in digital electronic circuitry, or in computer software, firmware, or hardware, including the structures disclosed in this specification and their structural equivalents, or in combinations of one or more of them. Some embodiments of subject matter described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A client and server are generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In the present disclosure, "each" refers to each of multiple items or operations in a group, and may include a subset of the items or operations in the group and/or all of the items or operations in the group. In the present disclosure, the term "based on" indicates that an item or operation is based at least in part on one or more other items or operations—and may be based exclusively, partially, primarily, secondarily, directly, or indirectly on the one or more other items or operations.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   using a measuring device to determine a result of adding a sample of a solid material to a test fluid, the test fluid comprising an additive; and
   determining a suitability of the additive for use in a stimulation treatment of a subterranean formation based on an adsorption characteristic of the additive determined from the result.

2. The method of claim 1, wherein using the measuring device to determine the result comprises:
   using the measuring device to measure a first surface tension of the test fluid before adding the sample to the test fluid; and
   using the measuring device to measure a second surface tension of the test fluid after adding the sample to the test fluid, wherein the result comprises a difference between the first surface tension and the second surface tension.

3. The method of claim 1, wherein using the measuring device to determine the result comprises:
   using the measuring device to measure a first contact angle between the test fluid and a test surface before adding the sample to the test fluid; and
   using the measuring device to measure a second contact angle between the test fluid and the test surface after adding the sample to the test fluid, wherein the result comprises a difference between the first contact angle and the second contact angle.

4. The method of claim 3, wherein measuring the second contact angle comprises measuring the second contact angle after a surface tension of the test fluid has reached a steady value.

5. The method of claim 3, wherein the second contact angle is greater than the first contact angle, and determining the suitability comprises determining that the additive is suitable for a proppant phase of the stimulation treatment.

6. The method of claim 1, wherein the test fluid comprises a first test fluid, the first test fluid comprises a first concentration of the additive in a solvent, the sample comprises a first sample, the result comprises a first result, and the method further comprises:
   using the measuring device to determine a second result of adding a second sample of the solid material to a second test fluid, the second test fluid comprising a second concentration of the additive and the solvent; and
   using the measuring device to determine a third result of adding a third sample of the solid material to a third test fluid, the third test fluid comprising a third concentration of the additive and the solvent;
   wherein the suitability is determined based on the first result, the second result, and the third result.

7. The method of claim 6, wherein the third concentration comprises a critical micelle concentration.

8. The method of claim 1, wherein the sample comprises at least one of granular rock material, granular mineral material, graded sand, a proppant material, cuttings from the subterranean formation, or crushed material from the subterranean formation.

9. The method of claim 1, wherein determining a suitability of the additive comprises using a data processor to analyze the result.

10. The method of claim 1, wherein determining a suitability of the additive comprises determining from the result that the additive is a non-adsorbing surfactant.

11. The method of claim 1, wherein determining a suitability of the additive comprises determining from the result that the additive is a weakly-adsorbing surfactant.

12. The method of claim 1, wherein determining a suitability of the additive comprises determining from the result that the additive is a strongly-adsorbing surfactant.

13. A method for performing a fracture treatment, the method comprising:
receiving information on an additive selected for treating a subterranean formation, the additive selected based on an adsorption characteristic determined from a measured result of adding a sample of a solid material to a test fluid comprising the additive; and
injecting the additive into the subterranean formation through a well bore defined in the subterranean formation.

14. The method of claim 13, wherein the sample comprises at least one of cuttings from the subterranean formation or crushed material from the subterranean formation.

15. The method of claim 13, wherein the subterranean formation comprises a first subterranean formation, and the sample comprises at least one of cuttings from a second subterranean formation or crushed material from a second subterranean formation.

16. The method of claim 13, wherein the sample comprises a volume of a proppant material, and injecting the additive comprises injecting the additive and the proppant material into the subterranean formation.

17. The method of claim 13, wherein the sample comprises a volume of a proppant material, and injecting the additive comprises injecting the additive into a region of the subterranean formation comprising the proppant material.

18. The method of claim 13, the additive selected based on at least one of:
the measured result of adding the sample to the test fluid comprising no change in a surface tension of the test fluid; or
the measured result of adding the sample to the test fluid comprising an increase in a contact angle of the test fluid and a test surface.

19. A system comprising:
a fluid testing subsystem that determines a suitability of an additive for a stimulation treatment based on an adsorption characteristic of the additive determined from a result of adding a sample of a solid material to a test fluid comprising the additive; and
a stimulation treatment subsystem that applies the additive to a subterranean formation through a well bore defined in the subterranean formation.

20. The system of claim 19, wherein the subterranean formation comprises shale and the well bore comprises a horizontal well bore.

21. The system of claim 19, wherein the subterranean formation comprises a formation matrix and a fracture network.

22. The system of claim 19, wherein the fluid testing subsystem comprises:
a fluid container that receives:
a test fluid comprising the additive; and
the sample of solid material; and
a tensiometer that measures a surface tension of the test fluid.

23. The system of claim 19, wherein the fluid testing subsystem comprises:
a fluid container that receives:
a test fluid comprising the additive; and
the sample of solid material; and
a contact angle goniometer that measures a contact angle between the test fluid and a test surface.

24. The system of claim 19, wherein the stimulation treatment subsystem comprises:
a tubular conduit installed in the well bore;
a pump that communicates a treatment fluid comprising the additive into the tubular conduit; and
an outlet in the well bore that receives the treatment fluid from the tubular conduit and communicates the treatment fluid into the subterranean formation.

* * * * *